US008211129B2

(12) United States Patent
Regadas

(10) Patent No.: US 8,211,129 B2
(45) Date of Patent: Jul. 3, 2012

(54) METHOD FOR ANASTOMOSIS SURGERY USING ZIP-TIES

(75) Inventor: Francisco Sergio Pinheiro Regadas, Fortaleza-Ceará (BR)

(73) Assignee: Unique Surgical Innovations LLC, Parkland, FL (US)

( * ) Notice: Subject to any disclaimer, the term of this patent is extended or adjusted under 35 U.S.C. 154(b) by 928 days.

(21) Appl. No.: 12/283,152

(22) Filed: Sep. 10, 2008

(65) Prior Publication Data

US 2009/0281560 A1     Nov. 12, 2009

Related U.S. Application Data

(60) Provisional application No. 61/126,615, filed on May 6, 2008.

(51) Int. Cl.
*A61B 17/11* (2006.01)
(52) U.S. Cl. ....................................................... 606/153
(58) Field of Classification Search .................. 606/153, 606/108; 227/175.1–182.1; 140/93 A, 123.6, 140/93.2; 248/74.3; 24/16 PB, 19, 20 TT; 128/898
See application file for complete search history.

(56) References Cited

U.S. PATENT DOCUMENTS

| 2,427,169 | A |   | 9/1947  | Wandel |          |
|-----------|---|---|---------|--------|----------|
| 3,683,926 | A |   | 8/1972  | Suzuki |          |
| 3,739,429 | A | * | 6/1973  | Kohke  | 24/16 PB |
| 4,592,354 | A | * | 6/1986  | Rothfuss | 227/179.1 |
| 4,640,320 | A | * | 2/1987  | Avison et al. | 140/93 A |
| 5,042,535 | A | * | 8/1991  | Schlottke | 140/93 A |
| 5,205,328 | A | * | 4/1993  | Johnson et al. | 140/93.2 |
| 5,314,435 | A | * | 5/1994  | Green et al. | 606/153 |
| 5,368,215 | A |   | 11/1994 | Green et al. |  |
| 5,417,702 | A |   | 5/1995  | Hempel |  |
| 5,549,619 | A | * | 8/1996  | Peters et al. | 606/151 |

(Continued)

FOREIGN PATENT DOCUMENTS

WO     WO 02/094109 A1     11/2002

(Continued)

OTHER PUBLICATIONS

N. Picardi, Original New Surgical Device-The "Grasping Tie" Its Use in Low Colo-rectal Anastomosis, Second International Scientific Teleconference "New Technology in Medicine", Saint-Petersburg, Russia, Mar. 2005, pp. 68-69.

(Continued)

*Primary Examiner* — Julian Woo
*Assistant Examiner* — Christopher L Templeton
(74) *Attorney, Agent, or Firm* — Melvin K. Silverman; Yi Li

(57) ABSTRACT

A double or triple zip-tied anastomosis surgery method is provided. The method includes circumferentially fastening a first and a second zip-tie around a tubular organ or a connecting region between two tubular organs, with the first and second zip-ties beside each other; dissecting the tubular organ or the connecting region at a space between the first and second zip-ties, forming a first tubular portion with a first zip-tied end and a second tubular portion with a second zip-tied end; resecting a target segment from the second tubular portion, and centrally fastened the resected end; then rejoining the first and the second tubular portions together using a circular stapler, with staples encircling the first zip-tied end and the centrally fastened resected end; and cutting and removing tissues and zip-tie encircled by the staples to recreate a tubular pathway, with a smooth interface between the two tubular portions.

12 Claims, 16 Drawing Sheets

U.S. PATENT DOCUMENTS

| | | | |
|---|---|---|---|
| 5,571,120 A | | 11/1996 | Yoon |
| 5,609,626 A | * | 3/1997 | Quijano et al. .............. 623/1.24 |
| 5,749,881 A | * | 5/1998 | Sackier et al. ................ 606/151 |
| 5,845,681 A | * | 12/1998 | Kurmis ........................ 140/93.2 |
| 6,152,936 A | | 11/2000 | Christy et al. |
| 6,368,340 B2 | | 4/2002 | Malecki et al. |
| 6,497,258 B1 | | 12/2002 | Flannery et al. |
| 7,131,970 B2 | | 11/2006 | Moses et al. |
| 7,284,731 B1 | * | 10/2007 | Johnson et al. ............. 248/74.4 |
| 2002/0111636 A1 | * | 8/2002 | Fleischman et al. .......... 606/139 |
| 2005/0228363 A1 | * | 10/2005 | Leiboff ........................ 604/541 |
| 2008/0302855 A1 | * | 12/2008 | Bilotti et al. ............... 227/179.1 |

FOREIGN PATENT DOCUMENTS

WO    WO2006/048905    *    5/2006

OTHER PUBLICATIONS

N. Picardi, A New Surgical Tool Facilitating the Low Colo-rectal Anastomosis. The Original "Grasping Tie", Ann. Ital. Chir., LXXV, 2, 2004.

* cited by examiner

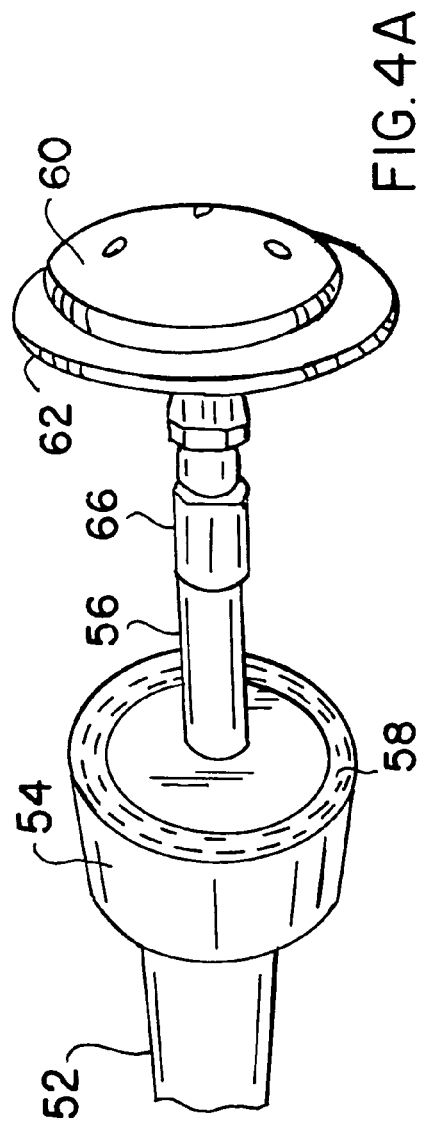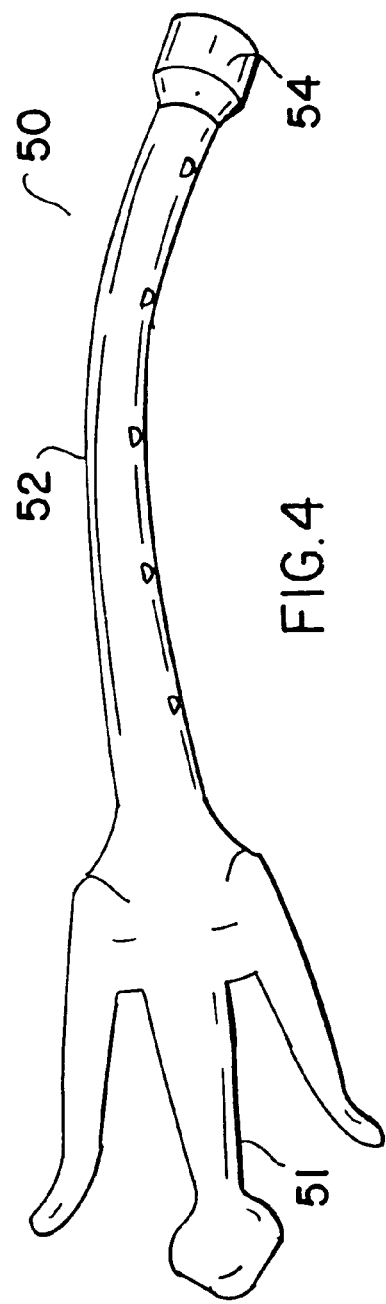

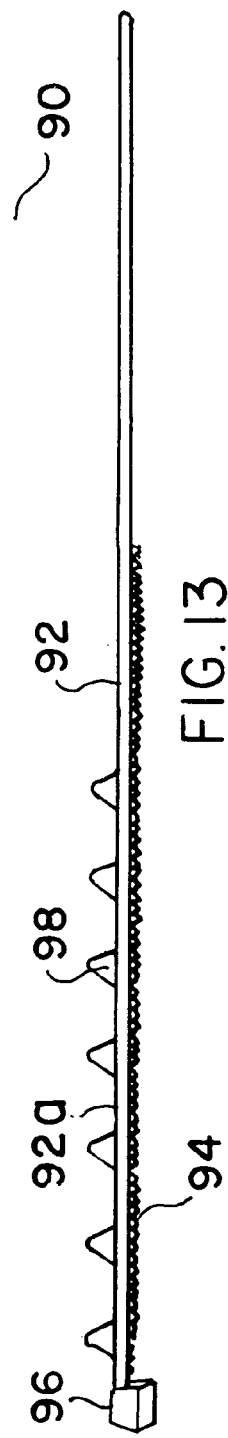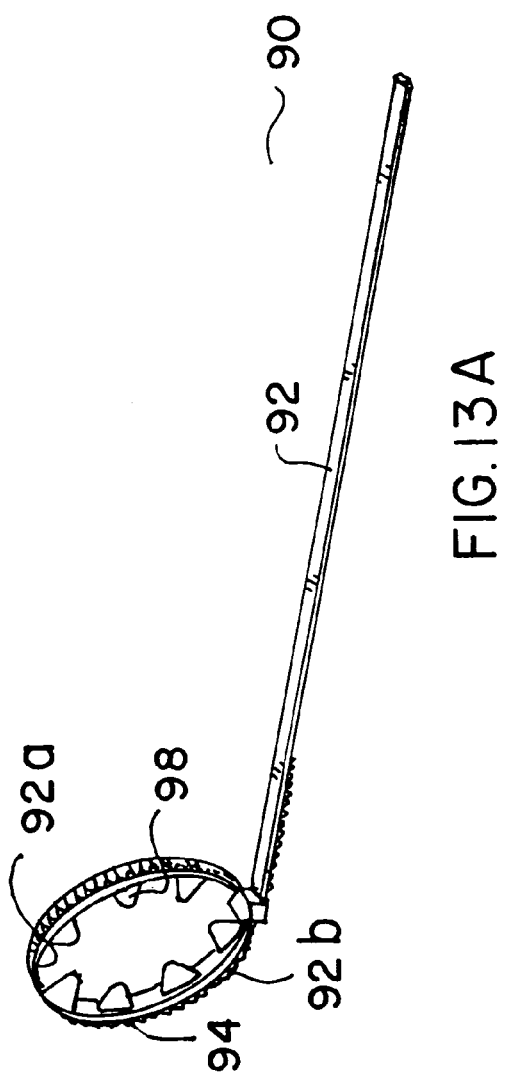
FIG.13
FIG.13A

METHOD FOR ANASTOMOSIS SURGERY USING ZIP-TIES

CROSS REFERENCE TO RELATED APPLICATION

This application claims the benefit under 35 USC 119(e) of the provisional patent application Ser. No. 61/126,615, filed May 6, 2008, which is herein incorporated by reference in its entirety.

FIELD OF THE INVENTION

The present invention relates to a method of anastomosis surgery using zip-ties, particularly relates to a zip-tied colorectal anastomosis surgery method.

BACKGROUND OF THE INVENTION

Surgical anastomosis is to join together two hollow organs, usually to restore continuity after resection, or less commonly to bypass an unresectable disease process. Anastomosis is typically performed on blood vessels including arteries and veins, gastrointestinal tract including esophagus, stomach, small intestine, colon, rectum, bile ducts and pancreas, urinary tract including ureters, urinary bladder and urethra, and fallopian tubes.

Colorectal anastomosis surgery is one of the most commonly performed intestinal surgical anastomosis ("Surgical Treatment of Rectal Cancer", Bleday R. et al, *The ASCRS Textbook of Colon and Rectal Surgery,* 2007, Springer, N.Y., page 413-436). Historically, laparotomies (open surgery) are performed. During the surgical procedure, after dissecting the colon from the rectum and resecting the diseased segment, such as cancerous tissue, from the colon, the two dissected open ends are manually sutured together. This is a time-consuming and often very difficult process. Particularly, when the diseased segment is located at the extreme low end of the rectum, which is deep in the lowest part of the pelvis, it can be extremely difficult to manually access the dissecting site. Under such circumstances, the surgery has a higher risk of anastomotic leakage, which causes severe infectious complications and often requires reoperation for an abscess, fistula, peritonitis, or a permanent colostomy (bringing the colon out through the abdominal wall so that waste can be collected in a bag rather than by evacuating stool through the anus).

In the past few decades, linear and circular surgical staplers have been developed and mechanically stapled methods are increasingly used in colorectal surgeries. The stapled colorectal anastomosis is faster and often more convenient for the surgeon to operate. However, various complications have been associated with stapled colorectal anastomosis. In the stapled colorectal anastomosis procedure, the linear and circular stapled areas overlap, which increases the risk of leakage at the interface between the linearly stapled area and the circularly stapled area. It has been reported in numerous publications that the instances of colorectal strictures in stapled anastomosis are statistically higher than in sutured colorectal anastomosis ("Stapled anastomosis after colorectal resection for benign and malignant disease", Raidoo, S N et al, S Afr Med J. 1984, 66(21):819-21; "Handsewn vs. stapled anastomosis in colon and rectal surgery: a meta-analysis", MacRae, H M et al, Dis Colon Rectum. 1998, 41(2):180-9; "Results of reoperations in colorectal anastomotic strictures", Schlegel R D et al, Dis Colon Rectum. 2001, 44(10): 1464-8; "Anastomotic dehiscence in colorectal surgery, Analysis of 1290 patients", Pronio, A et al, Chir Ital. 2007, 59(5): 599-609.)

More recently, laparoscopic colorectal anastomosis surgery method has been developed. With the laparoscopic method, a small cut is made on the lower abdomen, an endoscopic linear cutting stapler is inserted into pelvic cavity to transect the rectum, and a circular stapler is subsequently used to perform a colorectal colocolic, ileorectal, or ileoanal anastomosis. Laparoscopic colorectal anastomotic procedures have the advantages of a small wound, less trauma, and an overall faster patient recovery. However, the inherent problems from the stapled colorectal anastomosis remain in laparoscopic stapled anastomosis procedures. Furthermore, in laparoscopic colorectal anastomosis procedures, the head of the linear stapler can only be operated in a range from 0° to about 45° from the shaft. When the site for transection is in the distal rectum, it can be very difficult to transect the rectum with the linear cutting stapler. Typically, two or three sequential progressive stapling and cutting cartridges are required to transect the lower rectum. Each cut requires removing the stapler from the abdominal cavity and loading a new cartridge to the head of the stapler. This multifire approach is not only time consuming, but also a higher risk of complications and anastomotic leakage.

Therefore, there exists a strong need for improved tools and surgical methods to reduce the risks associated with existing sutured and stapling methods for anastomosis to improve operability under difficult conditions, to improve quality and outcome of the anastomosis and to reduce the cost of an anastomosis surgery.

SUMMARY OF THE INVENTION

In one aspect, the present invention is directed to a method of anastomosis surgery using zip-ties. In one embodiment, the method comprises fastening a first and a second zip-ties circumferentially around a tubular organ or a connecting region between two tubular organs, with the first and second zip-ties beside each other with a space therebetween sufficient for dissecting the tubular organ or the connecting region by a cutting edge; dissecting the tubular organ or the connecting region at the space between the first and second zip-ties, forming a first tubular portion with a first zip-tied end and a second tubular portion with a second zip-tied end; resecting a target segment from the second tubular portion, forming a resected end; placing one head member of a circular stapling device through resected end into the second tubular portion with a locking shaft of the one head member protruding from the resected end, and centrally fastening the resected end around the locking shaft of the one head member to form a centrally fastened resected end; placing another head member of the circular stapling device into the first tubular portion against the first zip-tied end, with a locking shaft of the another head member protruding from the first zip-tied end adjacent to the first zip-tie; joining the locking shafts and pulling the head members of the circular stapling device together with the first zip-tied end and centrally fastened resected end against each other; stapling the first tubular portion and the second tubular portion together, with staples encircling the first zip-tied end and the centrally fastened resected end; and cutting tissues encircled by the staples and removing cut tissues and the zip-tie to recreate a tubular path.

In the method, fastening the first and the second zip-ties includes fastening the zip-ties manually, or fastening the zip-ties mechanically by a zip-tie applicator; and dissecting at the space between the first and second zip-ties includes dissecting manually or dissecting with a blade disposed within the zip-tie applicator.

In a further embodiment, the method further includes fastening a third zip-tie circumferentially around the resected end onto the locking shaft of the another head member of the circular stapling device.

In a specific embodiment, the present invention is directed to a method of colorectal anastomosis surgery using zip-ties. The method comprises fastening a first and a second zip-ties circumferentially around rectum or sigmoid colon, with the first and second zip-ties beside each other with a space therebetween sufficient for insertion of a cutting edge; dissecting at the space between the first and second zip-ties, forming dissected rectum with a first zip-tied end and dissected colon with a second zip-tied end; resecting a target segment from the dissected colon, forming a resected end; placing one head member of the circular stapling device through the resected end into the colon with a locking shaft of the one head member protruding from the resected end, and centrally fastening the resected end around the locking shaft of the one head member to form a centrally fastened resected end; placing another head member of a circular stapling device into the dissected rectum against the first zip-tied end, with a locking shaft of the another head member protruding from the first zip-tied end adjacent to the first zip-tie; joining the locking shafts and pulling the head members of the circular stapling device together with the first zip-tied end and the centrally fastened resected end against each other; stapling the rectum and the colon together, with staples encircling the first zip-tied end and the centrally fastened resected end; and cutting tissues encircled by the staples and removing cut tissues and the zip-tie to recreate a colorectal path.

Furthermore, an intraluminal guide wire can also be used to guide the locking shaft of the another head member of the circular stapler for perforation adjacent to the zip-tie. The guide wire can be introduced from the anus through the first zip-tied end into the abdomen cavity using a rectoscope, or by penetrating through the zip-tied rectum from the abdomen cavity and exiting from the anus.

In a further aspect, the present invention provides surgical zip-ties and zip-tie applicators suitable to be used for the zip-tied anastomosis surgery of the present invention.

The advantages of the present invention will become apparent from the following description taken in conjunction with the accompanying drawings showing exemplary embodiments of the invention.

BRIEF DESCRIPTION OF THE DRAWINGS

FIG. 4 shows a circular stapler for colorectal anastomosis surgery. FIG. 4A shows the anvil and the head of the circular stapler joined through the anvil shaft and the center rod of the head.

FIGS. 13 and 13A show a zip-tie in another embodiment of the present invention in open and closed positions, respectively, wherein the inner surface of the zip-tie includes a plurality of protuberances at the head portion and the gear rack is disposed on the outer surface.

It is noted that in the drawings like numerals refer to like components.

DETAILED DESCRIPTION OF THE INVENTION

In one embodiment, the present invention provides a method of anastomosis surgery using zip-ties.

For the purpose of understanding and appreciating the differences of the method of the present invention from, and the advantages over, the prior art methods, the existing stapled and sutured colorectal anastomosis surgery methods are briefly described first in reference to drawings.

Figure 1:
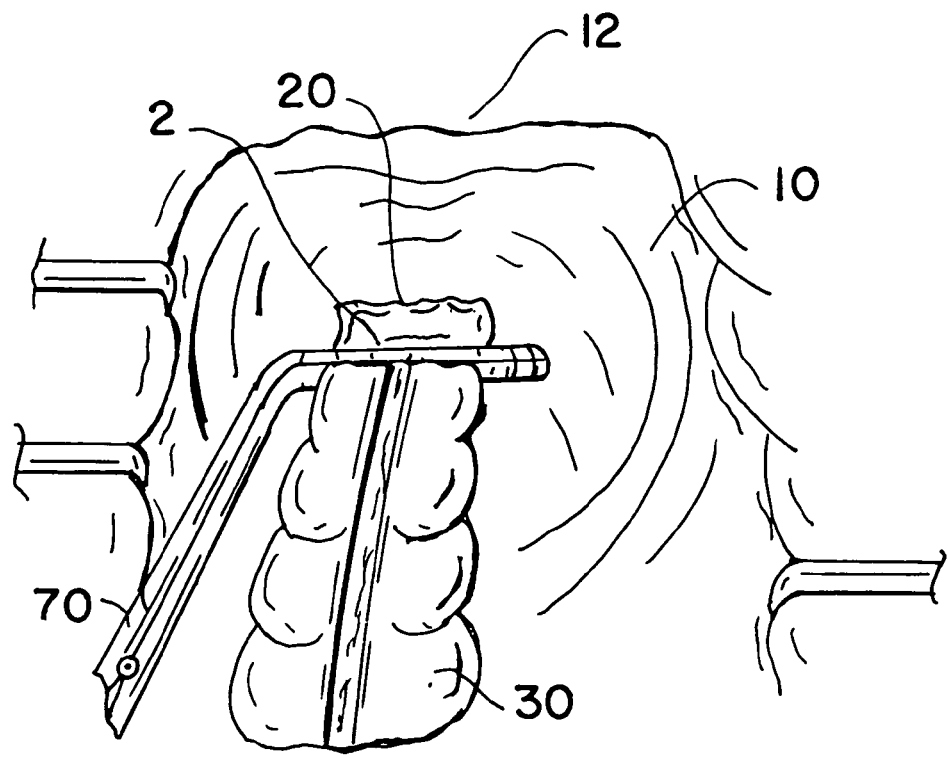
FIG. 1 illustrates the rectosigmoid region of a patient exposed in an open colorectal anastomosis surgery, with a clamp next to the dissecting site on the lower part of the rectum prior to anastomosis.

FIG. 1 illustrates the rectosigmoid region of a patient exposed in an open colorectal anastomosis surgery, with a clamp 70 clamping immediately next to the dissecting site 2 between the rectum 20 and the colon 30 in the lower pelvis cavity 10 behind the pubis 12.

Figure 2:
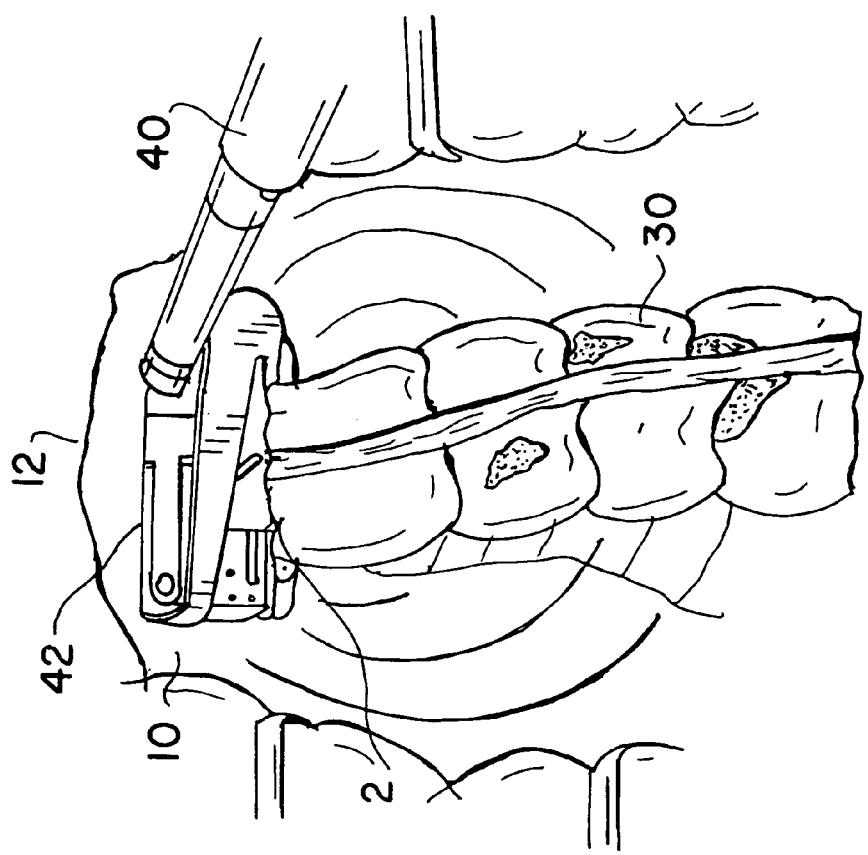
FIG. 2 illustrates transecting the rectum using a linear cutting stapler in a double or a triple stapling open rectosigmoid resection surgery.

In a double or a triple stapling open rectosigmoid resection procedure, a linear stapler 40 is used to close the rectum 20 and the colon 30 at the dissecting site 2, as shown in FIG. 2. The linear stapler has a head 42 which includes a disposable cartridge carrying staples. When the linear stapler is activated, it staples the tissue with two double rows of staples with a space therebetween. The dissecting site 2 is then transected in the space between the two double rows of staples. This can be performed manually by the surgeon using the superior edge of the staples as a guide. Alternatively, the dissecting site 2 can be mechanically transected using a linear cutting stapler that has a linear blade disposed between the two rows of staples. When the linear cutting stapler is activated, it staples the tissue with two parallel rows of staples first, and then dissects the tissue by the blade in the space between the two rows of the staples.

Figure 3:
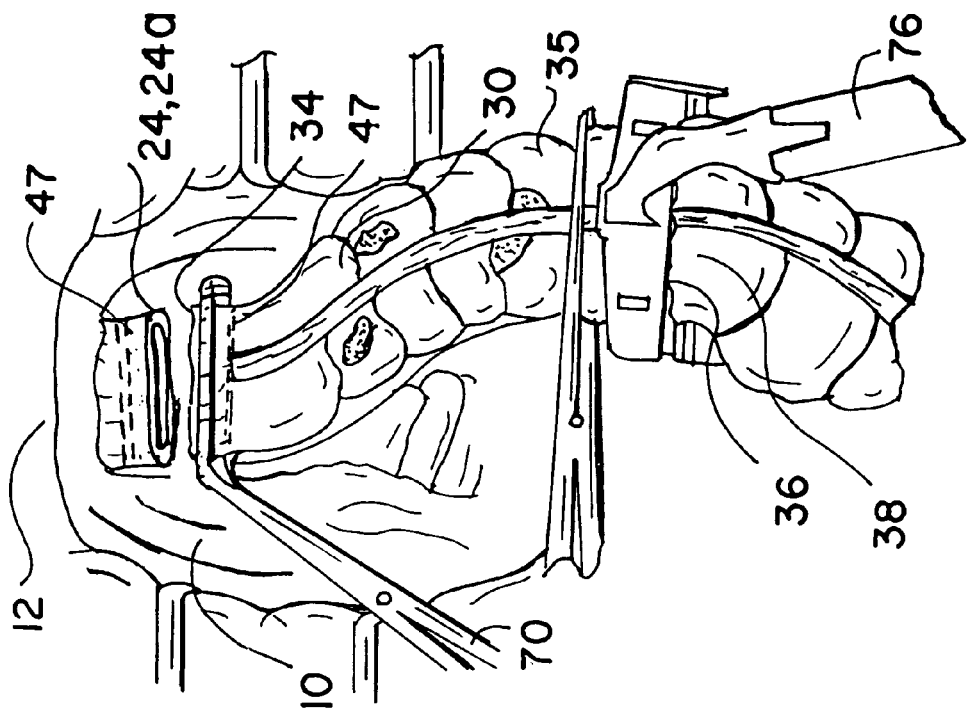
FIG. 3 illustrates resection of a target segment in the colon using a linear cutter.

As shown in FIG. 3, the dissection results in two free dissected ends, one dissected end 24 is a stapled linear closure 24a of the rectum 20, and the other dissected end 34 is a stapled linear closure of the colon 30. As further shown in FIG. 3, subsequently a target segment 35 in the colon 30, which may include a tumor or other abnormalities, is resected at a resecting site 36 by a linear cutter 76, which results in a resected end 38.

To rejoin the rectum and the colon after resection, a circular stapler is used. FIG. 4 illustrates a circular stapler 50 known in the art. Circular stapler 50 includes an elongated shank 52 with a handle 51 on one end and a cartridge 54 on the opposing end. As shown in FIG. 4A, cartridge 54 carries a plurality of staples arranged in a circle at the front end 58 of the cartridge. Extending forward from cartridge 54 is a center rod 56, which is herein also referred to as a locking shaft, adapted to interlock with an anvil shaft 66 (another locking shaft) of a removable anvil 60. When center rod 56 is interlocked with anvil shaft 66, anvil 60 can be pulled toward cartridge 54 until the surface 62 of anvil 60 against the front end 58 of cartridge 54. Since anvil 60 and cartridge 54 are two head members of a circular stapling device, and herein they are also referred to as one head member and another head member or vise versa.

Figure 5:
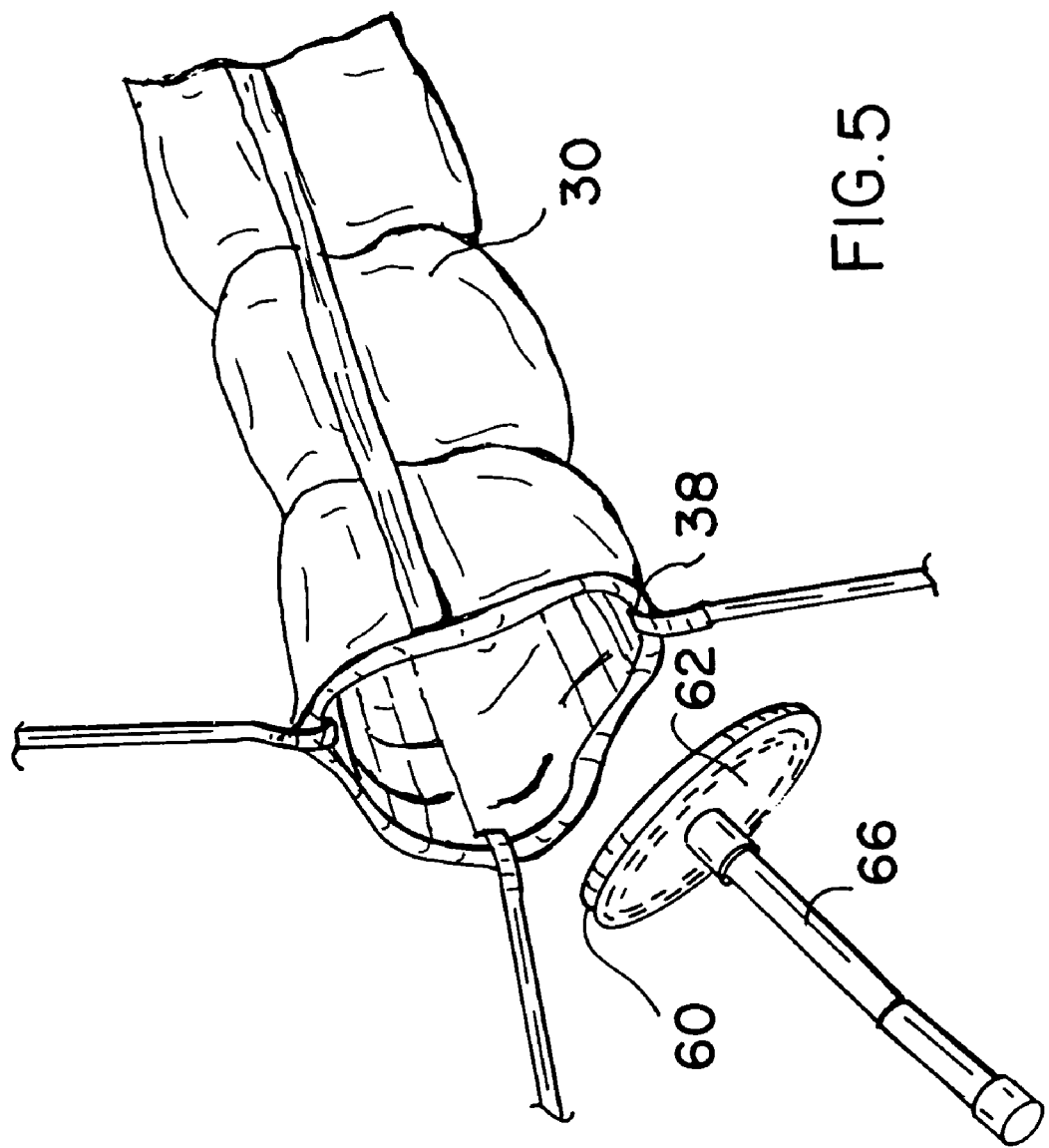
FIG. 5 illustrates after resection of the target segment, the anvil of the circular stapler is placed into the open proximal colon in a double or a triple stapling rectosigmoid resection surgery.
Figure 6:
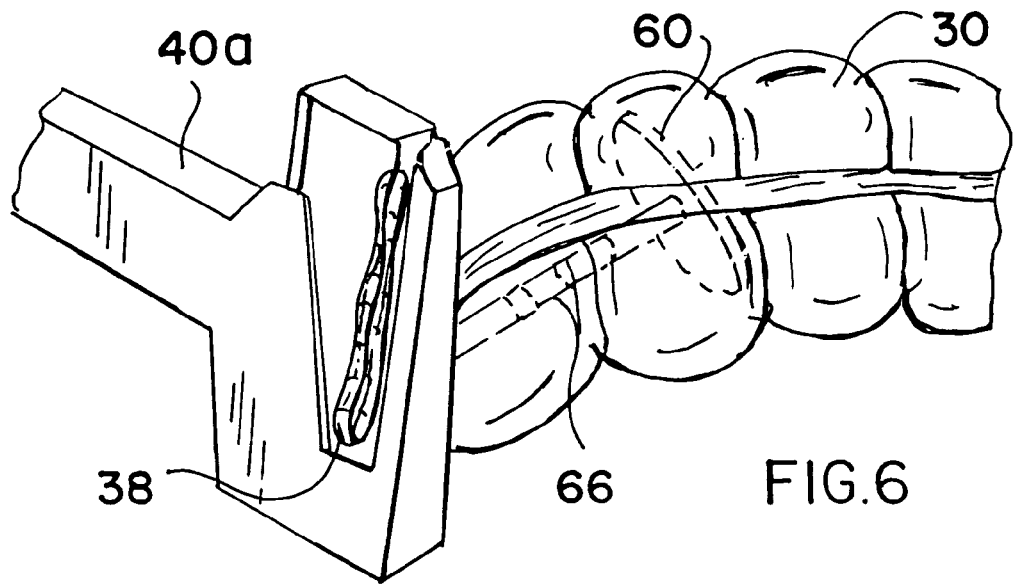
FIG. 6 illustrates the proximal colon containing the anvil is closed with a linear stapler.
Figure 6A:
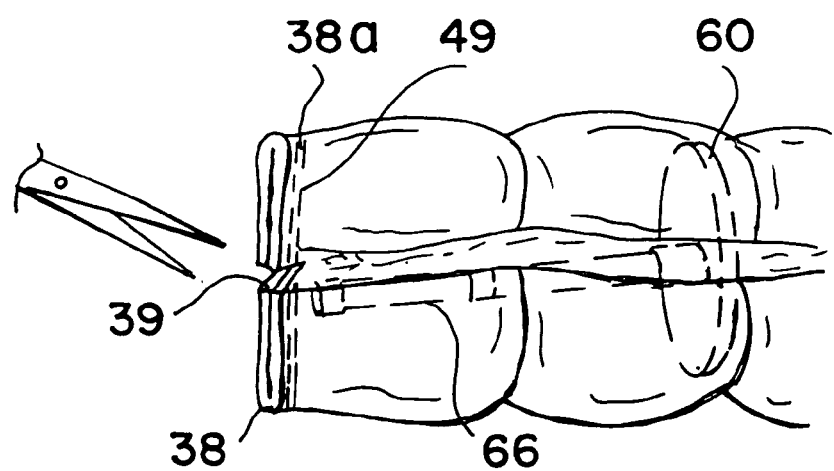
FIG. 6A illustrates a small incision is made at the midpoint of the stapled linear closure to retrieve the anvil shaft for a triple stapled procedure.

As illustrated in FIG. 5, to rejoin the rectum and the colon using circular stapler 50, anvil 60 is placed into the lumen of the colon 30 from the resected end 38. In the triple stapling colorectal anastomosis procedure, the resected end 38 is closed by a linear stapler 40a, which forms a linear closure 38a fastened by staples 49 as shown in FIGS. 6 and 6A. Anvil shaft 66 is pulled out from the stapled linear closure 38a through a small incision 39 at about the midpoint of the linear closure. Alternatively, in a double stapling colorectal anastomosis procedure, the resected end 38 is sutured onto anvil shaft 66 (see FIG. 9).

Figure 7:
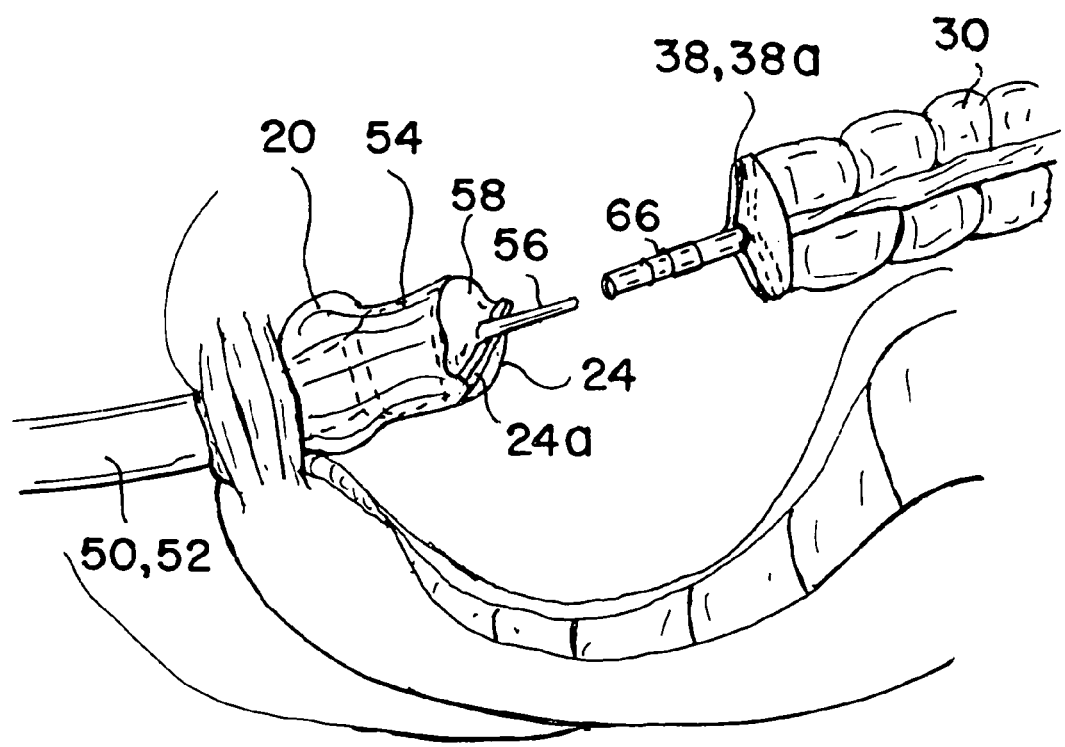
FIG. 7 illustrates that the head of the circular stapler is transanally placed into the rectum, and the tip of the center rod is advanced to perforate the rectal linear staple line at its midpoint.
Figure 8:
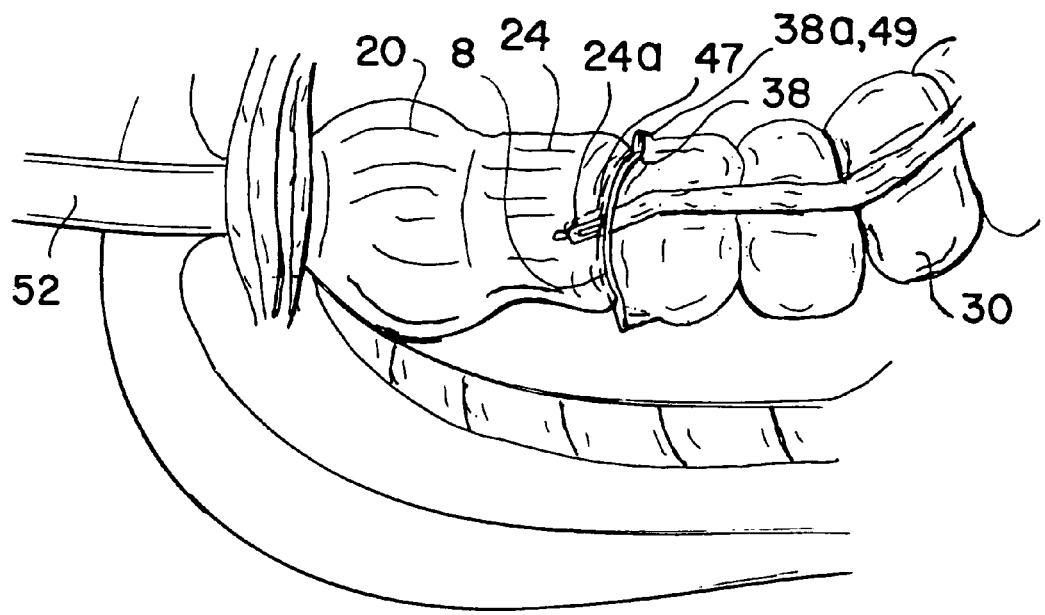
FIG. 8 illustrates that the anvil is closed against the stapling and cutting cartridge of the circular stapler. The colon is positioned so that the two linear staple lines are at right angles to one another in a cross-like mode.

On the other hand, as shown in FIG. 7, the cartridge 54 is transanally inserted into the rectum 20 and advanced to the extent that the front end 58 of cartridge 54 is positioned against the stapled linear closure 24a, and then center rod 56 is advanced to perforate the linear staple line about its midpoint. Center rod 56 and anvil shaft 66 are engaged and interlocked through a locking mechanism within (not shown). Then, anvil 60 is pulled toward the cartridge 54, along with the colon 30, until surface 62 of anvil 60 is against the front end 58 of cartridge 54, as shown in FIG. 8. As shown, the stapled linear closure 24a of dissected end 24 is horizontal, and the colon 30 is positioned to have the stapled linear closure 38a of resected end 38 in a vertical orientation, so that the two linear staple lines are at right angles to one another. The circular stapler 50 is activated to fasten dissected end 24 and resected end 38 together by placing a circular double staggered row of anastomosing staples, which results in a stapled circular closure 8 between the rectum 20 and the colon 30. Then, a circular blade disposed within cartridge 54 cuts through the colon and the rectum inside the double rows of staples, and the cartridge 54 is transanally removed together with anvil 60 and the cut tissues, which results in the recreated colorectal pathway, see FIG. 8A.

Figure 8A:
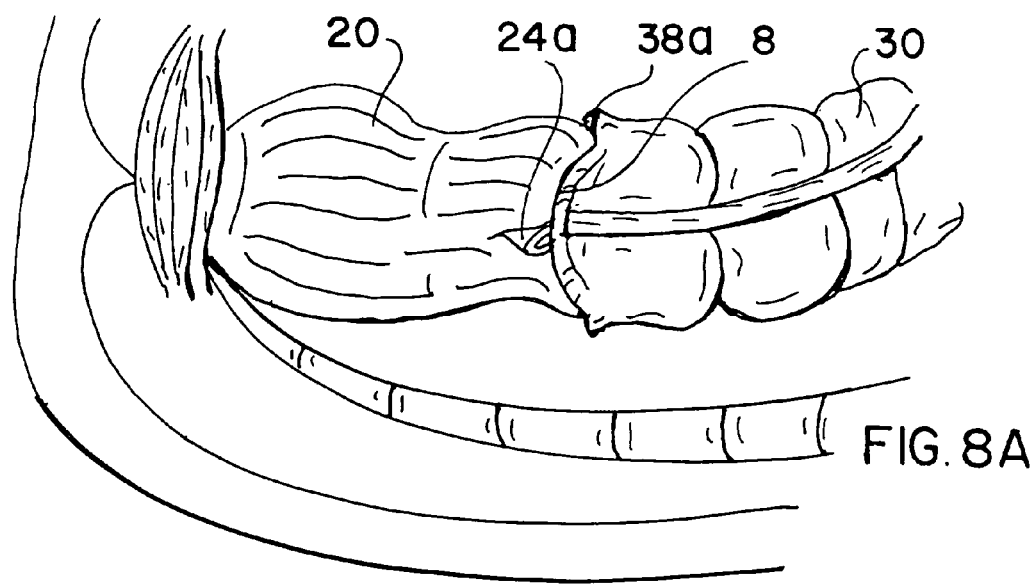
FIG. 8A illustrates the interface region between the rectum and the colon after the circular stapler is transanally retrieved, showing the overlap between the two stapled linear closures and stapled circular closure resulted from a triple stapling rectosigmoid resection procedure.

As shown in FIGS. 8 and 8A, in the triple stapling colorectal anastomosis procedure, the stapled circular closure 8 formed in the final step overlaps with the stapled linear closures 24a and the stapled linear closure 38a. The overlapped areas have higher risks of leakage and the tissues in the overlapped areas tend to scar, which may ultimately lead to stricture of the recreated pathway.

Figure 9:
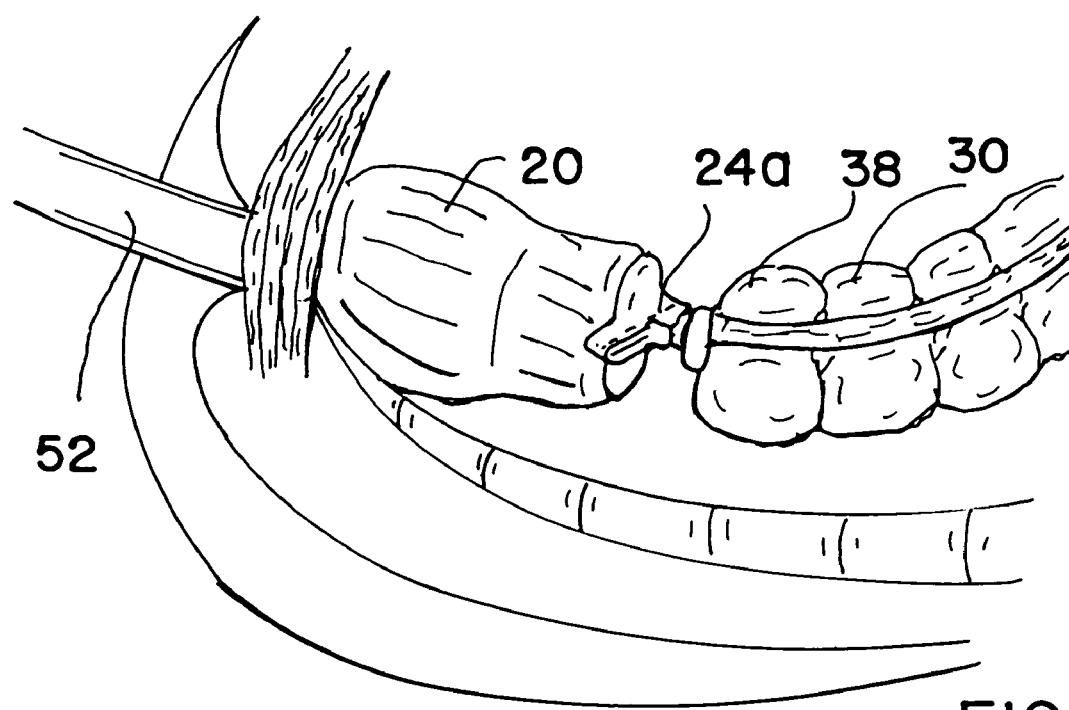
FIG. 9 illustrates the stapled linear closure of the rectum and sutured closure of the colon during a double stapling rectosigmoid resection procedure, when the anvil shaft and center rod of the circular stapler are joined, prior to the anvil being closed against the cartridge of the head.

FIG. 9 illustrates the stapled linear closure of the rectum and sutured closure of the colon during a double stapling rectosigmoid resection procedure, when the anvil shaft and center rod of the circular stapler are joined, prior to the anvil being closed against the cartridge of the head. As shown, in this procedure the resected end 38 is sutured onto anvil shaft 66, therefore, there is no stapled linear closure at the resected end 38. However, in the subsequent step of circular stapling, the stapled circular closure formed still overlaps with the stapled linear closure 24a. Therefore, the same issues discussed above in the triple stapling colorectal anastomosis procedure are present.

Figure 10:
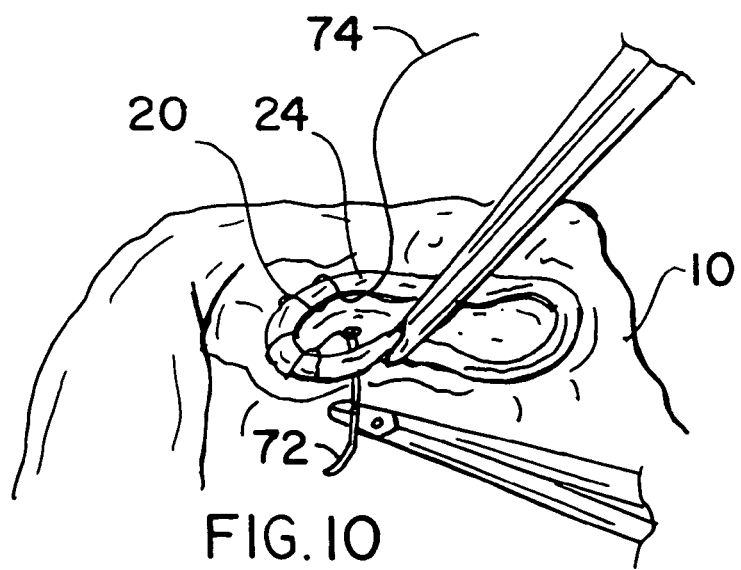
FIG. 10 illustrates manual suturing of the dissected end of the rectum stump to apply a traditional open manual purse-string.

In an open rectosigmoid resection procedure using manual suture without linear staplers, the colon 30 is dissected from the rectum 20 at the dissecting site 2 as shown in FIG. 1, by a linear cutter (not shown). The dissected end 24 is manually sutured by the surgeon using needle 72 and suture string 74 to close the rectal stump, as illustrated in FIG. 10. After resection of a target segment in the colon, a circular stapler is used to rejoin the rectum and the colon as described above. In this procedure, the resected end 38 is sutured onto anvil shaft 66, as described above in the double stapling rectosigmoid resection procedure. The cartridge 54 of circular stapler 50 is transanally placed into the rectum 20, and then the rectum 20 and the colon 30 are rejoined by circular stapling, as described above. In the manual sewn procedure, no stapled linear closure is present and hence the overlaps between the stapled linear closure and the stapled circular closure are avoided. However, as can be appreciated from FIG. 10, when the dissecting site 2 is located in the lower extreme of the pelvis cavity behind the pubis 12, manually suturing the dissected end 24 can be very difficult, and sometimes, it can be impossible. Due to poor accessibility, quality of suturing can be poor, which increases the risks of leakage and surgical complications.

The present invention overcomes the problems of existing surgical procedures by providing a method of zip-tying or zip-tied anastomosis surgery, which can be used for anastomosis surgery of various tubular organs, including the connection region between two tubular organs.

In one embodiment, the method is a double zip-tied procedure, which comprises the following steps:

(a) fastening a first and a second zip-ties circumferentially around a tubular organ or a connecting region between two tubular organs, with the first and second zip-ties beside each other with a space therebetween sufficient for dissecting the tubular organ or the connecting region by a cutting edge;

(b) dissecting the tubular organ or the connecting region at the space between the first and second zip-ties, forming a first tubular portion with a first zip-tied end and a second tubular portion with a second zip-tied end;

(c) resecting a target segment from the second tubular portion, forming a resected end;

(d) placing one head member of a circular stapling device through resected end into the second tubular portion with a locking shaft of the one head member protruding from the resected end, and centrally fastening the resected end around the locking shaft of the one head member to form a centrally fastened resected end;

(e) placing another head member of the circular stapling device into the first tubular portion against the first zip-tied end, with a locking shaft of the another head member protruding from the first zip-tied end adjacent to the first zip-tie;

(f) joining the locking shafts and pulling the head members of the circular stapling device together with the first zip-tied end and centrally fastened resected end against each other;

(g) stapling the first tubular portion and the second tubular portion together, with staples encircling the first zip-tied end and the centrally fastened resected end; and (h) cutting tissues encircled by the staples and removing cut tissues and the zip-tie to recreate a tubular path.

In a further embodiment, in step (f) fastening the resected end around the locking shaft of one head member is achieved by fastening a third zip-tie circumferentially around the resected end onto the locking shaft of one head member of the circular stapling device. As can be appreciated, this provides a triple zip-tied procedure.

Alternatively, centrally fastening the resected end around the locking shaft of the one head member is achieved by manually suturing the resected end around the locking shaft of the one head member of the circular stapling device.

Herein, the term "tubular organ" includes, but is not limited to, arteries, veins, esophagus, bile ducts, small intestine, colon, sigmoid colon, rectum, ureter, urethra, fallopian tube, and appendix. It should be understood that the first tubular portion and the second tubular portion resulted from the dissection can belong to the same tubular organ, or belong to two different tubular organs, depending on the location of the target segment and purpose of the surgery. For example, in a situation of a colon cancer patient with a tumor located in a middle portion of the colon, the first tubular portion and the second tubular portion are both a part of the colon, and the recreated tubular path is within the colon itself. However, in another situation of a colon cancer patient with the tumor located in the sigmoid colon, which is directly connected to the rectum, if the dissecting site 2 shown in FIG. 1 is at an upper portion of the rectum, the first tubular portion can be the rectum stump, and after resecting sigmoid colon, the remaining second tubular portion is the colon. Therefore, the recreated tubular path is between the rectum and the colon. In some extreme situations, small intestine may be connected to the rectum after resecting the colon.

Herein, the phrase "dissecting a tubular organ or a connecting region between two tubular organs" refers to, in most cases, transecting the tubular organ or the connecting region, which cuts the tubular organ in transverse to its longitudinal axis. However, "dissecting a tubular organ or a connecting region between two tubular organs" herein also includes cutting the tubular organ in an angle deviating from the transverse direction, which, sometimes, is required in an anastomosis procedure. Surgically, this action has also been referred to as dividing two tubular portions.

The term "target segment" refers to a segment of the tubular organ, or the connecting portion of two tubular organs, which is to be resected by the anastomosis surgery. Typically, the target segment includes abnormal tissue or abnormal organ structures affected by clinical conditions such as benign and malignant neoplasias of the digestive tract, unspecific inflammatory diseases of digestive tract such as ulcerative colitis and Crohn's disease, appendicitis, Meckel's diverticulitis, esophagus diverticulitis, Barrett's disease, obesity with metabolic disturbances, esophagus hernia, bile tract lithiasis, ureter stricture, and urethra stricture. In colorectal anastomosis surgery, the target segment typically include abnormal tissue or abnormal organ structures affected by conditions such as benign and malignant colorectal neoplasias, diverticular disease, megacolon, volvulus, ulcerative colitis, Crohn's disease, colorectal trauma, colorectal or pelvic endometriosis, Ischemic colitis, and anorectal abscess. However, the target segment may be normal tissue and organ structure. For example, in surgical treatment of functional diseases, modifying the bowel movement and producing chronic constipation, such as in treatment of colic inertia, a selected normal segment of the digestive tract needs to be resected.

Herein, the term "centrally fastening" refers to fastening the tubular organ toward the center of the longitudinal axis of the tubular organ. In contrast, a linear stapler fastens a tubular organ linearly in substantially transverse direction of the longitudinal axis of the tubular organ. The term "cutting edge" includes regular surgical blades, and a sharp edge or blade carried in surgical cutting devices.

Figure 11:
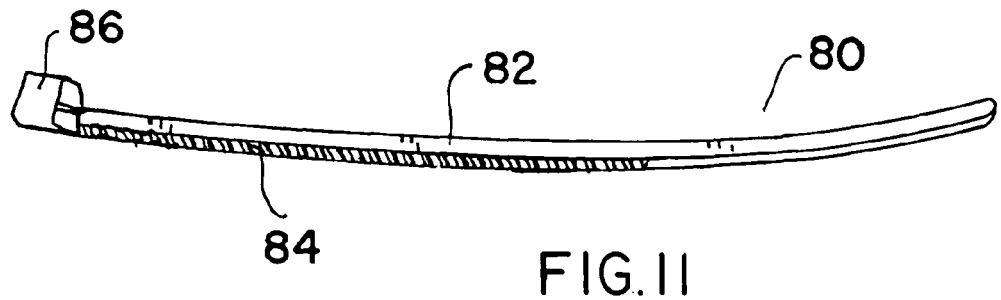
FIGS. 11 and 11A show a zip-tie in one embodiment of the present invention in open and closed positions, wherein the gear rack is disposed on the inner surface of the zip-tie.
Figure 11A:
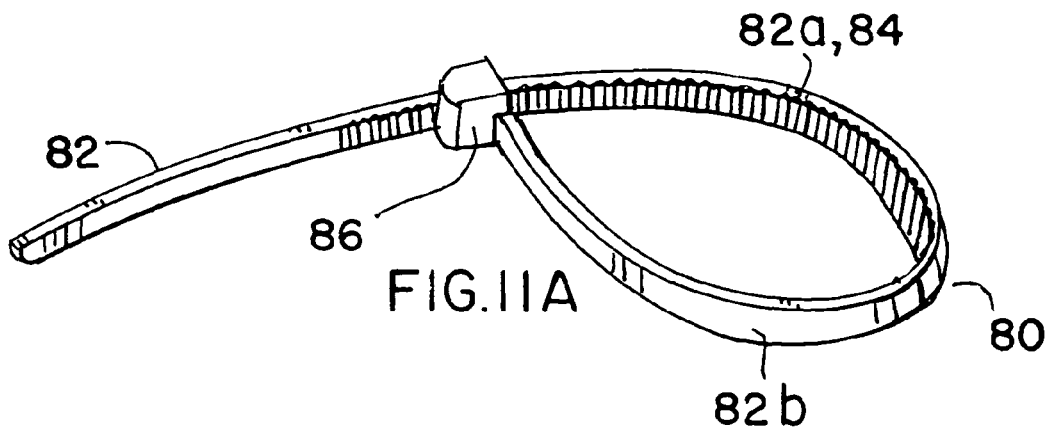

FIGS. 11 and 11A show a zip-tie 80 in one embodiment of the present invention, in an open and a closed configuration, respectively. Generally, structures and mechanisms of zip-ties are known in the art. In one embodiment, zip-tie 80 includes a sturdy strap 82 with an integrated gear rack 84 on one surface of the strap, and on one end a ratchet (not shown) within a small open case 86. Once the strap with the gear rack has been pulled through case 86 and past the ratchet, it is prevented from being pulled backward, and the resulting loop can only be pulled tighter in one direction. The dimensions of strap 82 may vary depending on the type of anastomosis surgery or the diameter of the tubular organ. For example, for colorectal anastomosis surgery, strap 82 may have a length from about 5 cm to about 10 cm, with a loop portion from about 1 cm to about 7 cm, a width from about 2 mm to about 5 mm, and a thickness from about 1 mm to about 4 mm. However, for artery anastomosis surgery, strap 82 may have a substantially shorter length.

As shown in FIG. 11A, the gear rack 84 is disposed on the inner surface 82a of strap 82, defined in reference to the locked loop. The gear rack may serve two functions. One function is a locking mechanism of the zip-tie as described above. Another function is to provide a textured surface inside the loop, which provides a certain level of friction or resistance between the tissue and the zip-tie to prevent potential sliding of the zip-tie when it is applied onto the tissue.

Figure 12:
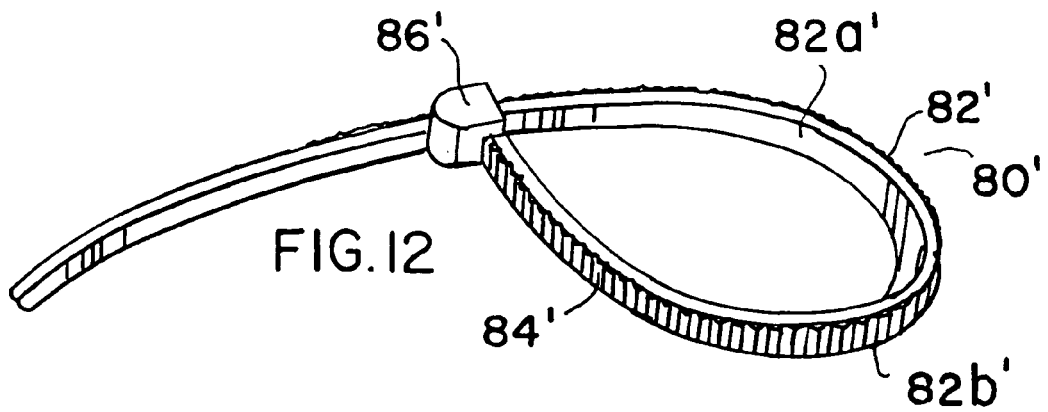
FIG. 12 shows a zip-tie in a further embodiment of the present invention in a closed position, wherein the inner surface of the zip-tie is smooth and the gear rack is disposed on the outer surface.

In an alternative embodiment, zip-tie 80' has the gear rack 84' integrated on the outer surface 82'b of strap 82', as shown in FIG. 12. In zip-tie 80', case 86' includes a ratchet (not shown) adapted to lock the gear rack on the outer side of the loop. In this embodiment, the inner surface 82a' of the loop is smooth, which is suitable for more fragile tissue type.

FIG. 13 shows a zip-tie 90 in a further embodiment. As shown, zip-tie 90 has gear rack 94 integrated on the outer surface 92b of strap 92. Moreover, strap 92 also includes multiple protuberances or ridges 98 on the inner surface 92a of strap 92 to provide a certain level of friction or resistance between the tissue and the zip-tie. In the embodiment shown, the protuberances are in a triangular-like shape, however, protuberances or ridges can have various suitable shapes and configurations. Alternatively, the inner surface 92 can have textured surface, such as grooves, indentations, pores, or surface roughness.

The zip-tie can be made of biocompatible materials, suitable for surgical use, and can be produced by plastic molding or other suitable methods known in the art. In one embodiment, the entire zip-tie including the case and the strap is made of one material. In another embodiment, the inner side and the outer side of the strap are made of two different materials. For example, the outer side is made of a more sturdy material to support the gear rack, and the inner side is made of a resilient material with surface roughness or textures. The two different sides can be joined together by heat, surgical adhesives, or other suitable materials or methods to form an integral strap. Suitable materials for making the zip-tie includes, but are not limited to, synthetic polymers, such as nylon, silicone, and other suitable surgical plastics.

The zip-tie can be either fastened circumferentially around the tubular organ manually, or mechanically using a zip-tie applicator in a laparotomy or laparoscopic procedure, or in a natural orifice procedure, such as insertion through the mouth, anus, vagina, urethra, or other natural orifice.

Figure 14:
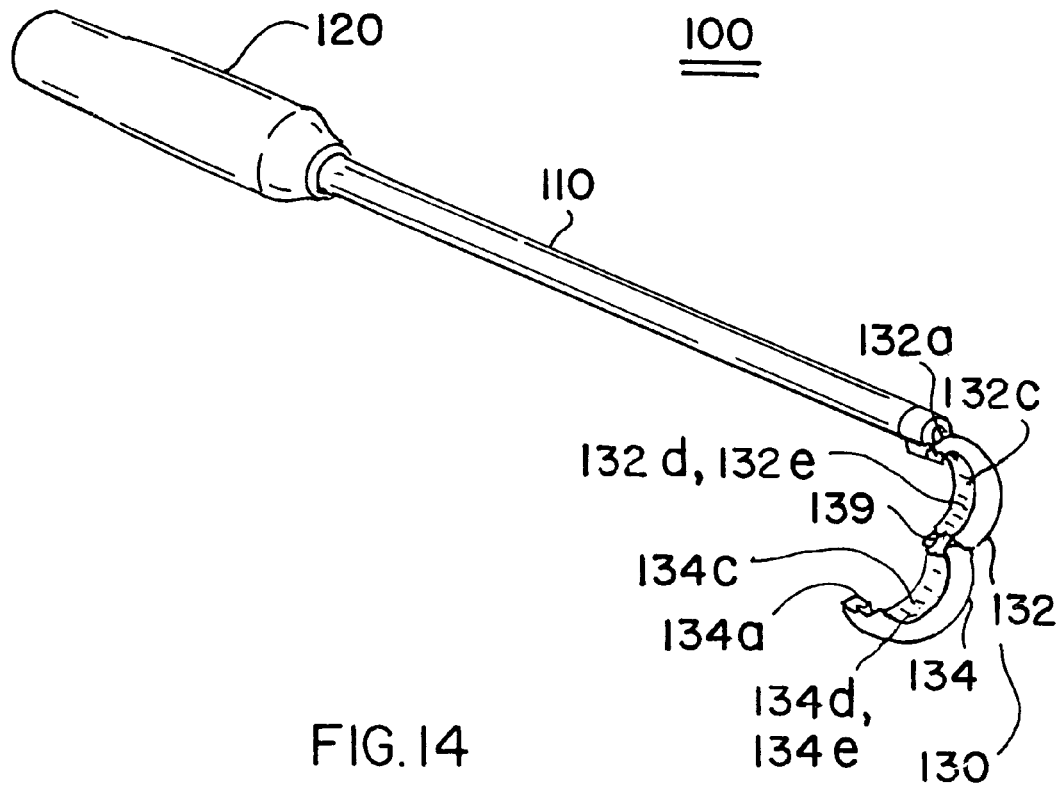
FIG. 14 shows an illustrative perspective view of a zip-tie applicator in one embodiment of the present invention.
Figure 14A:
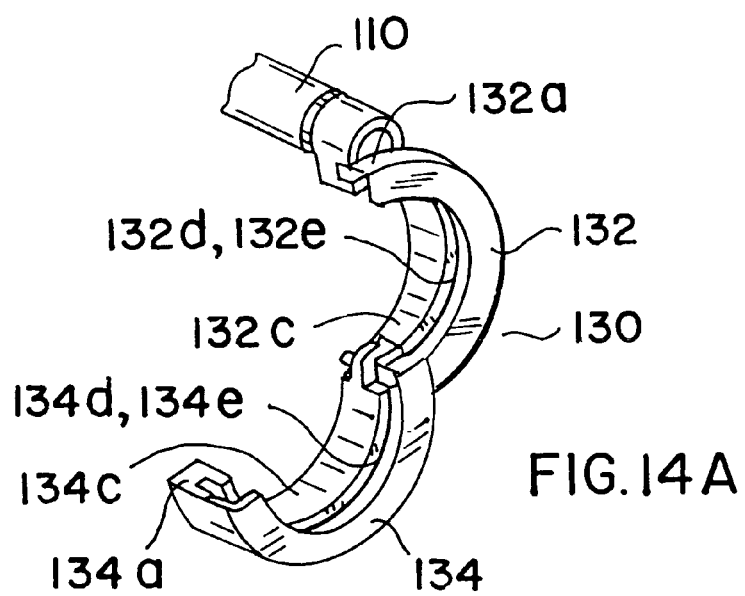
FIG. 14A shows an enlarged perspective view of the zip-tie tensioner of the applicator shown in FIG. 14.

FIG. 14 illustrates a zip-tie applicator in one embodiment of the present invention. As shown, zip-tie applicator 100 includes an elongated shaft 110, a handle 120 connected to shaft 110 on one end, and a zip-tie tensioner 130 connected to shaft 110 on the opposing end. In the embodiment shown, zip-tie tensioner 130 includes two semi-circular members 132 and 134 connected to each other by a hinge 139. The open end 134a of semi-circular member 134 can be attached to the fixed end 132a of semi-circular member 132, which forms a circular closure. The plane of semi-circular members 132 and 134 is at about 90 degree angle from the longitudinal axis of elongated shaft 110. On the interior side 132c of semi-circular member 132, there are two parallel grooves 132d and 132e, which are continued by parallel grooves 134d and 134e on the interior side 134c of semi-circular member 134. There is a distance between grooves 132d and 132e, as well as between 134d and 134e, sufficient for insertion of a cutting edge for dissecting tissue between two fastened zip-ties. When in use, two zip-ties are placed into the grooves, one in grooves 132d and 134d, and one in grooves 132e and 134e. When semi-circular member 134 is closed, a tensioning mechanism (not shown) disposed within the semi-circular members fastens the zip-ties, with a tubular organ tightened within. It is noted that various zip-tie tensioning mechanisms are known in the art, and can be used for zip-tie applicator of the present invention. Preferably, the tensioning mechanism is operated by a motor disposed with one of the semi-circular members. Furthermore, preferably, the zip-tie applicator further includes a strap cutting blade disposed within one of the semi-circular members, which is adapted to cut the strap after the zip-tie is fastened. Moreover, handle 120 can further include a control mechanism which is connected to zip-tie tensioner 130 through shaft 110.

In a further embodiment, the zip-tie applicator can further include two semi-circular blades (not shown) disposed in semi-circular members 132 and 134 between grooves 132d and 132e, and grooves 134d and 134e respectively. When two zip-ties are fastened as described above, the two blades can be activated by the motor to dissect the tubular organ fastened by the zip-ties.

FIGS. 15 thru 18 illustrate an example of the zip-tied anastomosis surgery method of the present invention, using zip-tie applicator 100 in an open rectosigmoid resection surgery.

Figure 15:
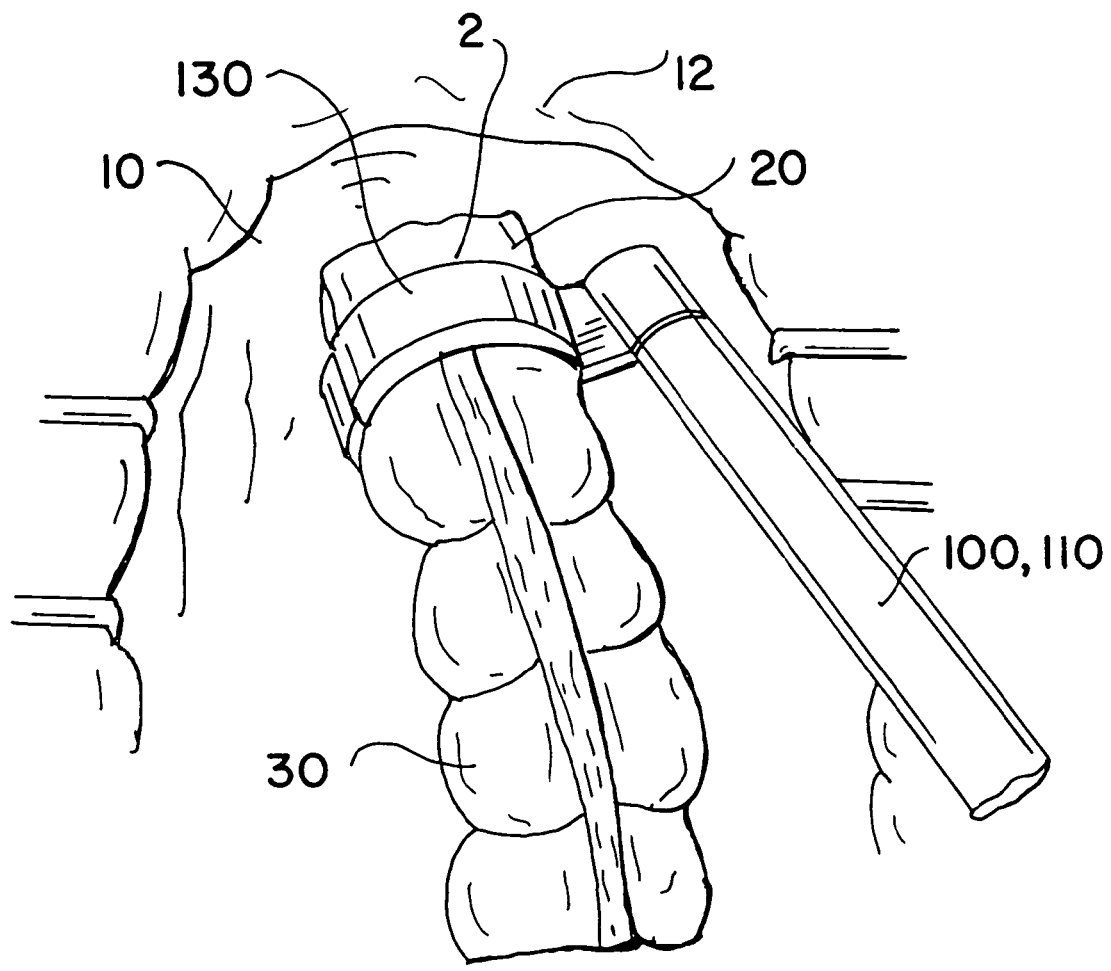
FIG. 15 illustrates the use of the zip-tie applicator shown in FIG. 14 in an open rectosigmoid resection procedure, with the zip-tie tensioner of the applicator wrapping around the rectum at the dissecting site to fasten the rectum circumferentially using two zip-ties carried within the tensioner.
Figure 16:
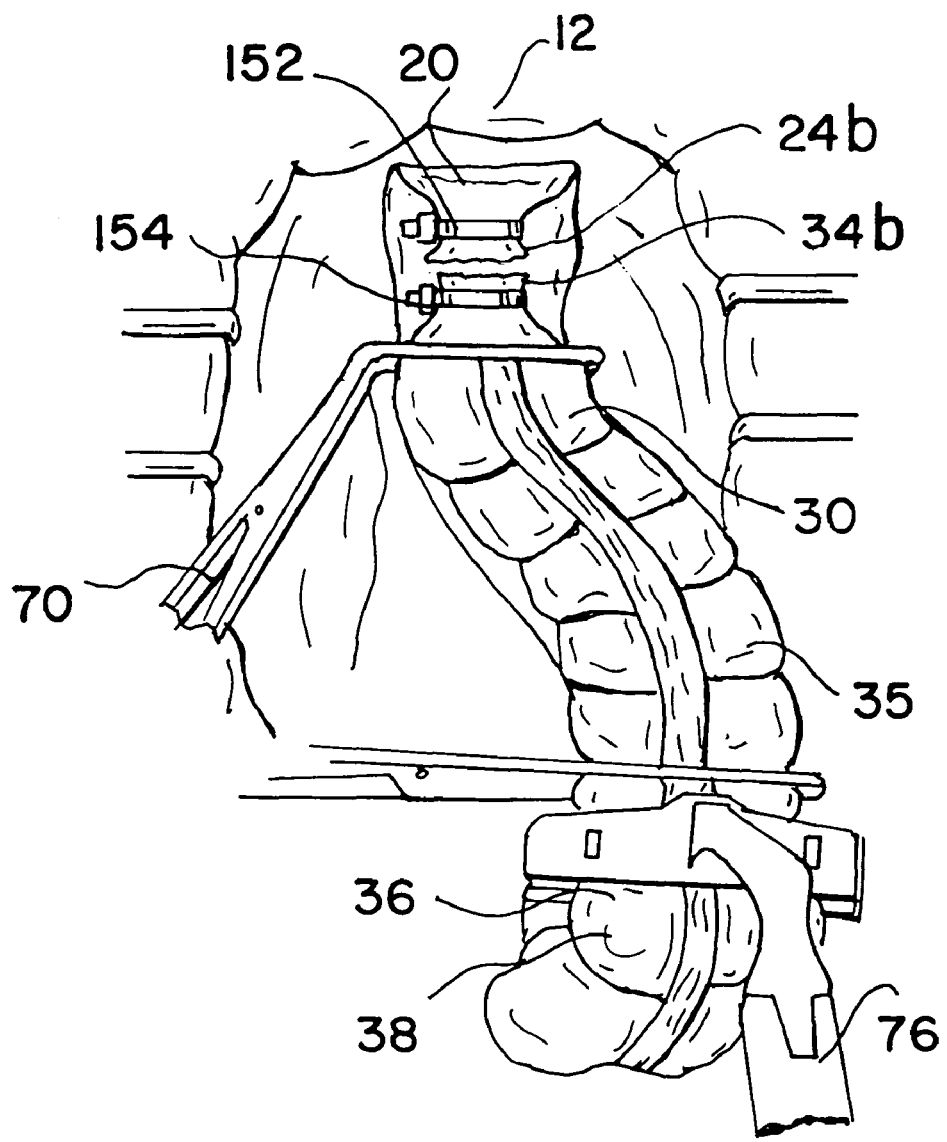
FIG. 16 illustrates two zip-tied ends after transecting the rectum, and resection of a target segment in the colon.

As illustrated in FIGS. 15 and 16, in an open rectosigmoid resection surgery, after the rectosigmoid region is exposed following the existing surgical procedure, semi-circular members 132 and 134 of zip-tie tensioner 130 of zip-tie applicator 100 is placed around the rectum 20 at a selected dissecting site 2. Zip-tie tensioner 130 carries two zip-ties therein. Zip-tie applicator 100 is activated using a control mechanism on the handle to fasten two zip-ties circumferentially around the rectum 20 in parallel. Then, zip-tie applicator is triggered again to dissect the rectum 20 in the space between the two fastened zip-ties 152 and 154 using the blades carried with the semi-circular members. Alternatively, zip-tie applicator 100 is removed after fastening the zip-ties, and the rectum 20 is manually dissected in the space between the two fastened zip-ties 152 and 154 by the surgeon. As shown in FIG. 16, this results in two zip-tied dissecting ends, one zip-tied end 24b is a zip-tied closure of the rectum stump, and the other zip-tied end 34b is a zip-tied closure of the colon 30. As further shown in FIG. 16, subsequently the target segment 35 in the colon 30 is resected at a resecting site 36, either by a linear cutter 76 or other surgical blades, which results in a free resected end 38.

After resection, the rectum 20 and the colon 30 are rejoined using an existing circular stapler. It is noted that for the purpose of the present invention, various commercially available circular staplers, such as DST circular staplers manufactured by United States Surgical (Norwalk, Conn.) and CDH circular staplers manufactured by ETHICON ENDO-SURGERY (Cincinnati, Ohio) can be used.

Figure 20:
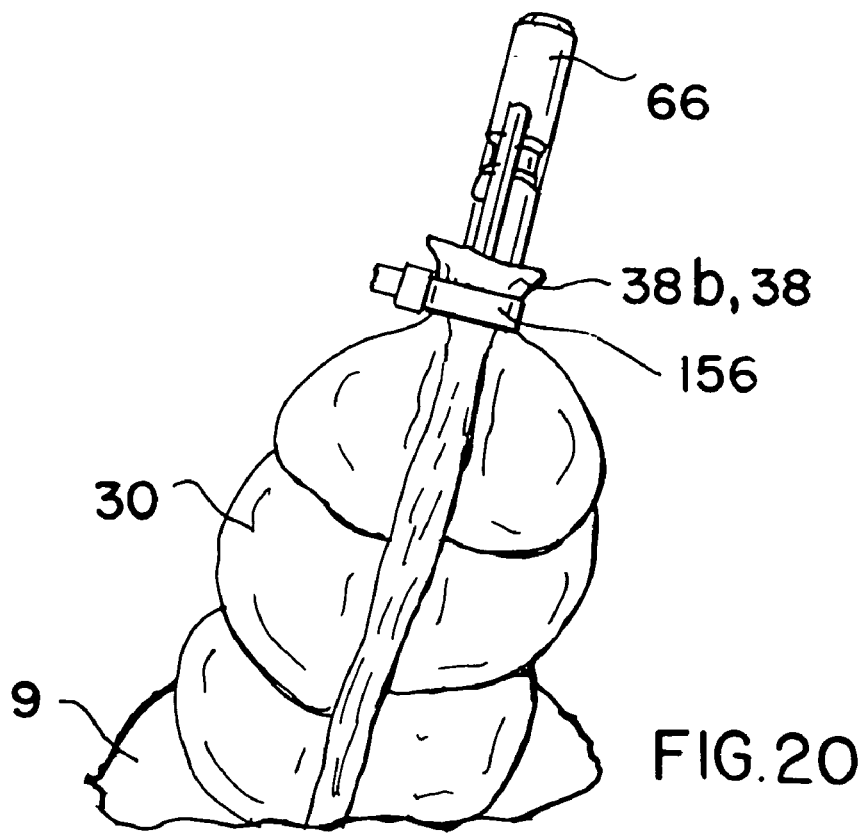
FIG. 20 illustrates the zip-tied resected end of the colon with the anvil placed with the proximal colon and the anvil shaft remaining outside of the colon, prior to placing the colon back into the pelvis cavity.

As illustrated in FIG. 5, anvil 60 is placed into the lumen of the colon 30 from the resected end 38 with anvil shaft 66 remaining outside of resected end 38. Then, the resected end 38 is centrally fastened. Preferably, a third zip-tie 156 is fastened circumferentially around resected end 38, which fastens the colon 30 onto anvil shaft 66 to form a zip-tied resected end 38b, as shown in FIG. 20. The third zip-tie can be fastened either manually by the surgeon or using a zip-tie tensioner. This zip-tie tensioner may have the same or different structure from zip-tie tensioner 130 of zip-tie applicator 100. To fasten resected end 38 onto the anvil shaft only one zip-tie is needed. Moreover, the resected end 38 can be more readily accessed by the surgeon in either open surgery or laparoscopic surgery, therefore, the elongated shaft of zip-tie applicator 100 is not needed. Alternatively, resected end 38 can be tied around anvil shaft 66 by purse-string suture. Using either the third zip-tie or purse-string suture, the method forms a centralized closure.

Figure 17:
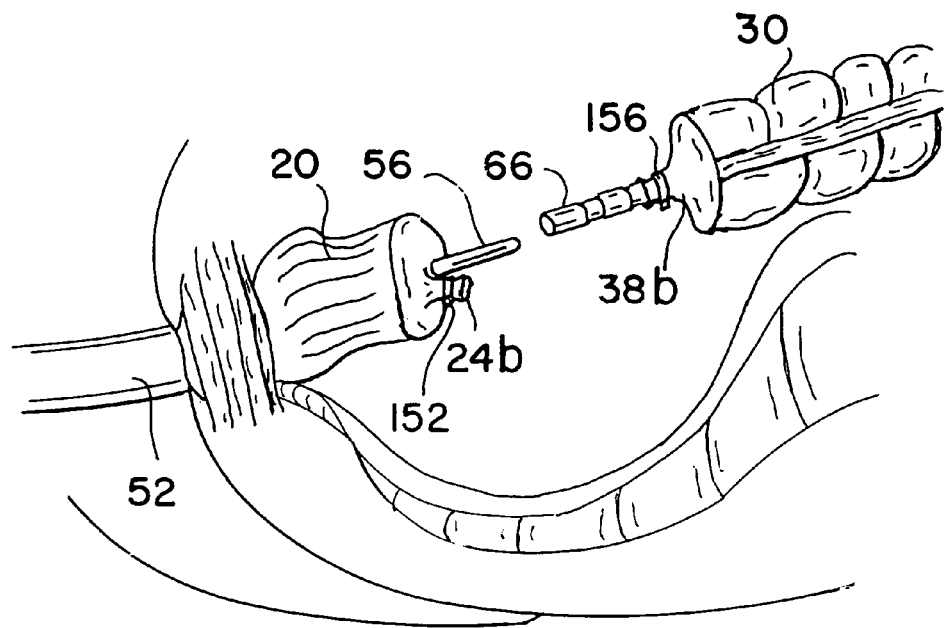
FIG. 17 illustrates that the head of the circular stapler carrying the stapling and cutting cartridge is transanally inserted into the rectum, and the tip of the center rod is advanced to perforate zip-tied closure adjacent to the zip-tie.

Then, cartridge 54 of circular stapler 50 carrying stapling and cutting cartridge 58 is transanally inserted in the rectum 20 and advanced to the extent that cartridge 58 is positioned against the zip-tied end 24b, and then center rod 56 is advanced to perforate the zip-tied closure adjacent to the zip-tie, as shown in FIG. 17 (cartridge 54 is within the rectum 20 in FIG. 17). The point of perforation should be sufficiently close to the zip-tie, which is at the center of the zip-tied closure, so long as the zip-tie does not interfere with the connection between the center rod and the anvil shaft. To position the center rod adjacent to the zip-tie assures the zip-tied end to be enclosed within the circle of the staples.

Figure 17A:
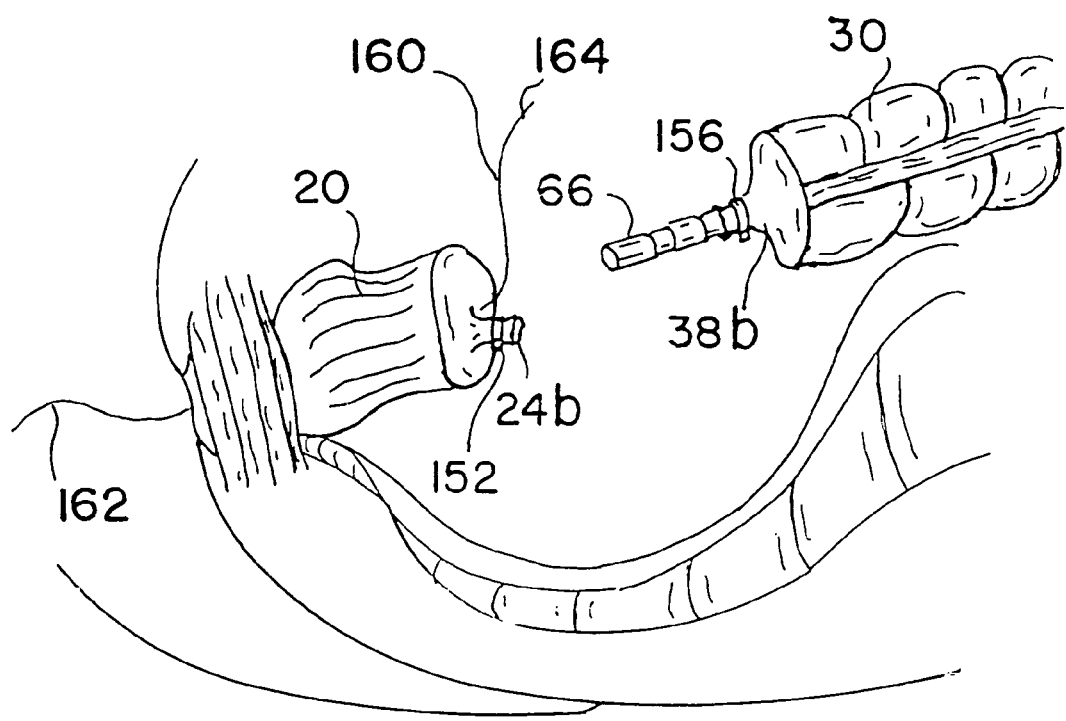
FIG. 17A illustrates that a guide wire is introduced into the rectum first with the distal end thereof remaining outside of the anus and the proximal end thereof in the abdomen cavity, before the distal end of the guide wire is fastened to the center rod of the circular stapler for guiding the center rod to perforate the zip-tied closure adjacent to the zip tie.

Optionally, an intraluminal guide wire can also be used to guide the center rod for perforation adjacent to the zip-tie. In rectosigmoid resection surgery, either laparotomic or laparoscopic procedure, sometimes it is difficult for the surgeon to see the position of the fastened closure of the rectum stump when advancing the center rod. To assure that the center rod perforates adjacent to the zip-tie, an intraluminal guide wire can be first introduced into the zip-tied rectum stump. The guide wire can be introduced from the abdomen cavity or through the anus. In one embodiment, as shown in FIG. 17A, a guide wire 160 is introduced from the abdomen cavity into the rectum by penetrating the distal end 162 of guide wire 160 through the zip-tied closure at a point adjacent to the zip-tie and the distal end 162 is taken out from the anus by the surgeon. Alternatively, the distal end 162 can also penetrate the zip-tied closure through the loop of the zip-tie. The distal end 162 is then fastened to center rod 56 of circular stapler 50. After the cartridge 54 of circular stapler 50 is inserted into the rectum 20 transanally, the center rod 56 is advanced in a direction guided by the guide wire 160. The guide wire 160 is pulled from its proximal end 164 by the surgeon, which assures that the center rod perforates the zip-tied closure adjacent to the zip-tie.

In another embodiment, the guide wire can be introduced transanally, which is particularly suitable for the situations of high colorectal anastomosis. In this embodiment, a flexible or rigid rectoscope can be inserted in the rectum through anus carrying guide wire 160 within. The proximal end 164 of guide wire 160 penetrates the zip-tied closure at a point adjacent to the zip-tie or through the loop of the zip-tie, and the proximal end 164 is pulled up from the abdomen cavity and the rectoscope is retrieved, with the distal end 162 remaining outside the anus, as shown in FIG. 17A. Then, the distal end 162 is fastened to center rod 56 of circular stapler 50. After the cartridge 54 of circular stapler 50 is inserted into the rectum 20 transanally, the center rod 56 is advanced in a direction guided by the guide wire 160, which perforates the zip-tied closure adjacent to the zip-tie. The guide wire is a flexible, thin wire made of metal, polymer, or other suitable surgical plastic materials. As can be appreciated from the above description, depending on the direction of penetration, either the distal end or the proximal end of the guide wire can be referred to as the first end or the second end.

Figure 18:
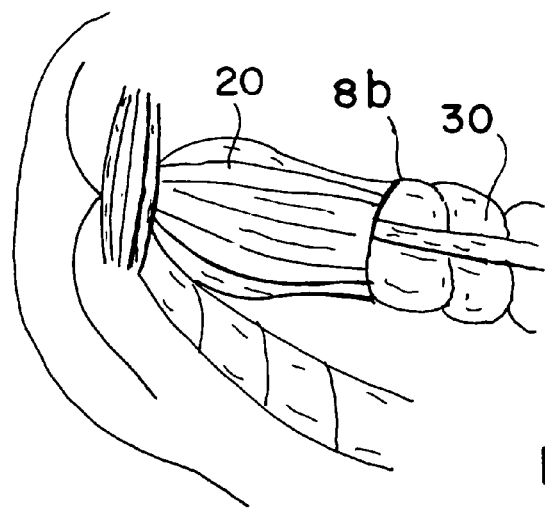
FIG. 18 illustrates the interface region between the rectum and the colon after the circular stapler is removed, showing a smooth circular closure between the rectum and the colon.

After center rod 56 is properly positioned, center rod 56 and anvil shaft 66 are engaged and interlocked through the locking mechanism between the center rod and the anvil shaft. Anvil 60 (within the colon 30) is pulled toward cartridge 54, along with the colon 30, until surface 62 of anvil 60 is against cartridge 58 (see FIG. 4A also). Then, circular stapler 50 is activated to staple the rectum 20 and the colon 30 together by placing a circular double staggered row of anastomosing staples, with the staples encircling zip-tied end 24b and zip-tied resected end 38b. This forms stapled circular closure 8b between the rectum 20 and the colon 30, as shown in FIG. 18. Then, the circular blade disposed within cartridge 54 cuts through the colon and the rectum inside the double rows of staples, and cartridge 54 is removed transanally together with anvil 60, the cut tissues and the zip-tie, which results in a smooth recreated colorectal pathway.

As shown in FIG. 18, using the zip-tied colorectal anastomosis procedure, the stapled circular closure 8b formed in the final step has a smooth interface between the rectum 20 and the colon 30. The areas of tissues being stapled are fresh and intact, absent any stitches or staples. Therefore, it substantially reduces the risks of leakage at the interface region and surgical complications. Since no overlap between different closures, such as those present in double and tripling stapling anastomosis procedures, the zip-tied colorectal anastomosis procedure has the advantages of less tissue scarring, and consequently less stricture of the recreated pathway.

As can be understood, this type of circular stapled interface can also be achieved using manual suturing procedure, where both the dissected end 24 of the rectum and the resected end 38 of the colon are manually sutured as shown in FIG. 10 and FIG. 9, respectively. However, as described earlier, manually suturing the dissected end 24 of the rectum is a very difficult process and often impossible to perform. Using the zip-tied colorectal anastomosis procedure of the present invention, the rectum can be readily fastened by zip-ties. Particularly, with the assistance of the zip-tie applicator, even the lower portion of the rectum can be readily fastened and dissected. This process has the advantage of shorter surgery time of the existing double or triple stapling anastomosis procedures, yet free of the inherent disadvantages of linear stapling methods.

The zip-tied anastomosis method can also be used in trans-abdominal end-to-end colorectal anastomosis procedure, which typically has the dissecting site at a higher portion of the rectum. In this surgical procedure, after initial dissection using double zip-ties as described above, the zip-tied dissected end 24 of the rectum can be reopened by cutting off the zip-tied portion, then anvil 60 of the circular stapler is placed into reopened dissected end 24 and the dissected end 24 is centrally fastened by a third zip-tie, with anvil shaft 66 staying outside. After resection of the target segment in the colon, the resected end 38 of the proximal colon is centrally fastened by a fourth zip-tie. An incision is made on the wall of the colon, and the cartridge 54 of the circular stapler is inserted into the colon through the incision, with the cartridge 58 placed against the zip-tied resected end, and the center rod 56 perforating the zip-tied closure adjacent to the zip-tie. Then, the center rod and the anvil shaft are joined and the anvil shaft is closed against the cartridge. The circular stapler is then activated to staple the rectum and the colon together, which forms stapled smooth circular closure, as described above. In this procedure, after cutting the tissues encircled inside the staples, the head together with the anvil, cut tissues and the zip-ties are removed from the incision on the wall of the colon, and the incision is closed by purse-string suture.

Figure 19:
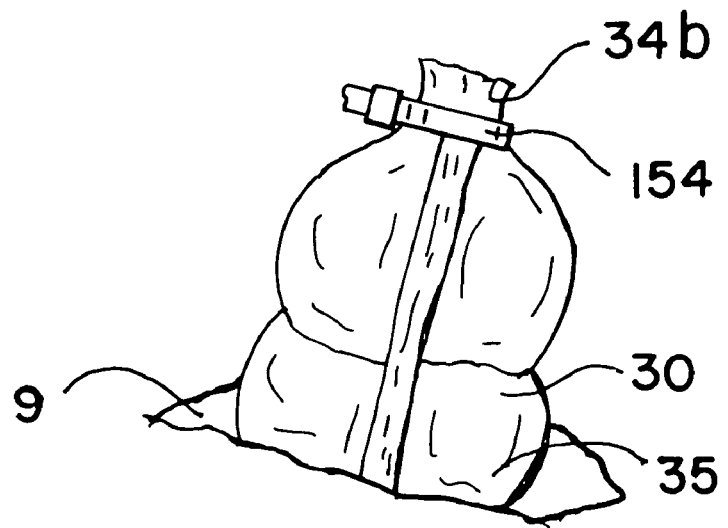
FIG. 19 illustrates the zip-tied transected end of the colon taken out from the small incision on the abdomen before resection of the target region.

Furthermore, the zip-tied anastomosis method can be used in laparoscopic surgery. In laparoscopic surgery within the abdominal or pelvic cavities, a small incision is made on the abdomen of a patient, and then a zip-tie applicator can be inserted into the pelvic cavity to dissect the colon from the rectum as described above in the open surgery, which is monitored using a laparoscope. After dissection, the zip-tied end 34b of the colon 30 is taken out from the pelvic cavity through the small incision 9, as shown in FIG. 19. Then, as described in the open surgery procedure, the target segment 35 is resected, which forms a resected end 38. The circular stapler 50 is used to rejoin the colon and the rectum. As shown in FIG. 20, anvil 60 is placed into the proximal colon, and resected end 38 is fastened by a third zip-tie 156 onto anvil shaft 66. Then, the zip-tied colon is placed back into the pelvis cavity through the small incision 9. As described previously in the open surgery and shown in FIG. 17, the cartridge 54 of the circular stapler 50 is inserted into the rectum 20 transanally, and placed against the zip-tied end 24b with the center rod 56 perforating the zip-tied closure adjacent to the zip-tie.

Then, center rod 56 and anvil shaft 66 are joined, and the anvil is closed against the cartridge. The circular stapler is then activated to staple the rectum 20 and the colon 30 together, which forms stapled smooth circular closure, as described above. After cutting the tissues encircled inside the staples by the circular stapler, the head, together with the anvil, cut tissues and the zip-ties are removed from anus, which forms the recreated colorectal pathway. The small incision on the abdomen is then closed by purse-string suture.

For laparoscopic zip-tied anastomosis surgery, the zip-tie applicator may have a different structure. The zip-tie tensioner may comprise two semi-circular members, with one end of both semi-circular members pivotally attached to the elongated shaft. The semi-circular members are adapted to open and close as controlled by the control mechanism on the handle. Moreover, the two semi-circular members may also connect to the elongated shaft by a second pivot, which enables the plane of the semi-circular members to be adjusted at a desired angle when the zip-tie tensioner is advanced inside the pelvis cavity to the dissecting site.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What is claimed is:

1. A method of anastomosis surgery using zip-ties, comprising:
   (a) placing a zip-tie tensioner of a zip-tie applicator circumferentially around a tubular organ or a connecting region between two tubular organs, said zip-tie tensioner containing therein a first and a second zip-tie disposed in parallel, and fastening said first and second zip-ties circumferentially around said tubular organ or said connecting region between two tubular organs, thereby having said first and second zip-ties fastened beside each other with a space therebetween sufficient for dissecting said tubular organ or said connecting region by said cutting edge;
   (b) dissecting said tubular organ or said connecting region at said space between said first and second zip-ties with a blade disposed within said zip-tie applicator, forming a first tubular portion with a first zip-tied end and a second tubular portion with a second zip-tied end;
   (c) resecting a target segment from said second tubular portion, forming a resected end;
   (d) placing one head member of a circular stapling device through said resected end into said second tubular portion with a locking shaft of said one head member protruding from said resected end, and centrally fastening said resected end around said locking shaft of said one head member to form a centrally fastened resected end;
   (e) placing another head member of said circular stapling device into said first tubular portion against said first zip-tied end, with a locking shaft of said another head member protruding from said first zip-tied end adjacent to said first zip-tie;
   (f) joining said locking shafts and pulling said head members of said circular stapling device together with said first zip-tied end and centrally fastened resected end against each other;
   (g) stapling said first tubular portion and said second tubular portion together, with staples encircling said first zip-tied end and said centrally fastened resected end; and
   (h) cutting tissues encircled by said staples and removing cut tissues and said zip-tie to recreate a tubular path.

2. The method of claim 1, wherein said centrally fastening said resected end around said locking shaft of said one head member includes fastening a third zip-tie circumferentially around said resected end onto said locking shaft of said one head member of said circular stapling device.

3. The method of claim 1, wherein said centrally fastening said resected end around said locking shaft of said one head member includes manually suturing said resected end around said locking shaft of said one head member of said circular stapling device.

4. The method of claim 1, wherein said tubular organ includes arteries, veins, esophagus, bile ducts, small intestine, colon, sigmoid colon, rectum, ureter, urethra, fallopian tubes, or appendix.

5. The method of claim 1, wherein said first tubular portion is the rectum, and said second tubular portion is the colon.

6. The method of claim 1, wherein said target segment includes normal or abnormal tissue, normal or abnormal organ structure.

7. The method of claim 1, wherein said cutting tissues encircled by said staples includes cutting tissues with a circular blade disposed within one of said heads of said circular stapling device.

8. A method of colorectal anastomosis surgery using zip-ties, comprising:
   (a) placing a zip-tie tensioner of a zip-tie applicator circumferentially around rectum or sigmoid colon, said zip-tie tensioner containing therein a first and a second zip-tie disposed in parallel, and fastening said first and second zip-ties circumferentially around said rectum or sigmoid colon, thereby having said first and second zip-ties fastened beside each other with a space therebetween sufficient for insertion of said cutting edge;
   (b) dissecting at said space between said first and second zip-ties with a blade disposed within said zip-tie applicator, forming a dissected rectum with a first zip-tied end and a dissected colon with a second zip-tied end;
   (c) resecting a target segment from said dissected colon, forming a resected end;
   (d) placing one head member of a circular stapling device through said resected end into said colon with a locking shaft of said one head member protruding from said resected end, and centrally fastening said resected end around said locking shaft of said one head member to form a centrally fastened resected end;
   (e) placing another head member of said circular stapling device into said dissected rectum against said first zip-tied end, with a locking shaft of said another head member protruding from said first zip-tied end adjacent to said first zip-tie;
   (f) joining said locking shafts and pulling said head members of said circular stapling device together with said first zip-tied end and said centrally fastened resected end against each other;
   (g) stapling said rectum and said colon together, with staples encircling said first zip-tied end and said centrally fastened resected end; and
   (h) cutting tissues encircled by said staples and removing cut tissues and said zip-tie to recreate a colorectal path.

9. The method of claim 8, wherein said centrally fastening said resected end around said locking shaft of said one head member includes fastening a third zip-tie circumferentially around said resected end onto said locking shaft of said one head member of said circular stapling device.

10. The method of claim 8, wherein said centrally fastening said resected end around said locking shaft of said one head member includes manually suturing said resected end around said locking shaft of said one head member of said circular stapling device.

11. The method of claim 8 further comprising, before step (e), introducing a guide wire into said dissected rectum from the anus, with a first end of said guide wire penetrating said first zip-tied end through, or adjacent to, said first zip-tie, with a second end of said guide wire staying outside the anus; fastening said second end of said guide wire to said locking shaft of said another head member; and then during said placing said another head member of said circular stapling device into said dissected rectum, guiding said locking shaft of said another head member to perforate said first zip-tied end adjacent to said first zip-tie by pulling said first end of said guide wire from the abdomen cavity.

12. The method of claim 8 further comprising, before step (e), introducing a guide wire into said dissected rectum from the abdomen cavity with a first end of said guide wire penetrating said first zip-tied end through, or adjacent to, said first zip-tie, and receiving said first end outside of the anus; fastening said first end of said guide wire to said locking shaft of said another head member; and then during said placing said another head member of said circular stapling device into said dissected rectum, guiding said locking shaft of said another head member to perforate said first zip-tied end adjacent to said first zip-tie by pulling said second end of said guide wire from the abdomen cavity.

* * * * *